United States Patent [19]

Bujan

[11] 3,960,149

[45] June 1, 1976

[54] FLOW CONTROL DEVICE

[75] Inventor: Albert Frank Bujan, Waukegan, Ill.

[73] Assignee: Abbott Laboratories, North Chicago, Ill.

[22] Filed: Nov. 13, 1974

[21] Appl. No.: 523,294

[52] U.S. Cl. .......................... 128/214 R; 24/115 L; 24/132 WL; 251/6; 251/9
[51] Int. Cl.² ...................... A61M 5/14; F16K 7/06
[58] Field of Search ............................. 251/4, 6–10; 24/115 L, 132 R, 132 WL, 134 E, 134 EA, 136 A, 244; 128/21 RR, 214.2

[56] References Cited
UNITED STATES PATENTS

| | | | |
|---|---|---|---|
| 2,167,952 | 8/1939 | Jordan | 251/7 |
| 2,595,511 | 5/1952 | Butler | 251/6 |
| 2,804,092 | 8/1957 | Aitchison | 251/9 X |
| 2,865,038 | 12/1958 | Versteeg | 251/9 X |
| 3,099,429 | 7/1963 | Broman | 251/4 X |
| 3,497,175 | 2/1970 | Koland | 251/9 |
| 3,544,060 | 12/1970 | Stoltz et al. | 251/9 |
| 3,685,787 | 8/1972 | Adelberg | 251/6 |
| 3,724,818 | 4/1973 | Roger | 251/9 |

*Primary Examiner*—Martin P. Schwadron
*Assistant Examiner*—Richard Gerard
*Attorney, Agent, or Firm*—Robert L. Niblack; Neil E. Hamilton

[57] ABSTRACT

A flow control device for accurately regulating the flow of fluid through flexible tubing. A pivotal platen is employed in conjunction with a roller which upon rotation along an intersecting axis with a length of tubing will effect a squeezing or compressive action on the tubing but with the compressive force being applied over a wide area of the tubing so as to not effect a distortion of the tubing after the compressive force is discontinued. The flow control unit can be utilized as a clamp in that it can completely disrupt the flow of fluid through the tubing yet it is highy adapted to being used as a flow control device in conjunction with a parenteral administration set.

16 Claims, 9 Drawing Figures

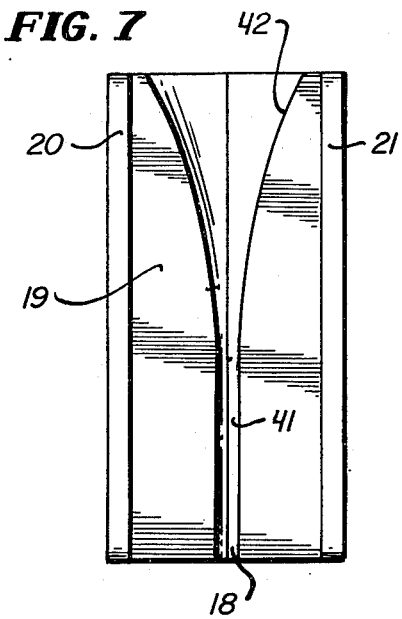
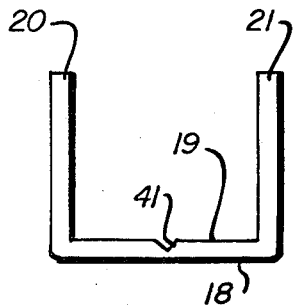
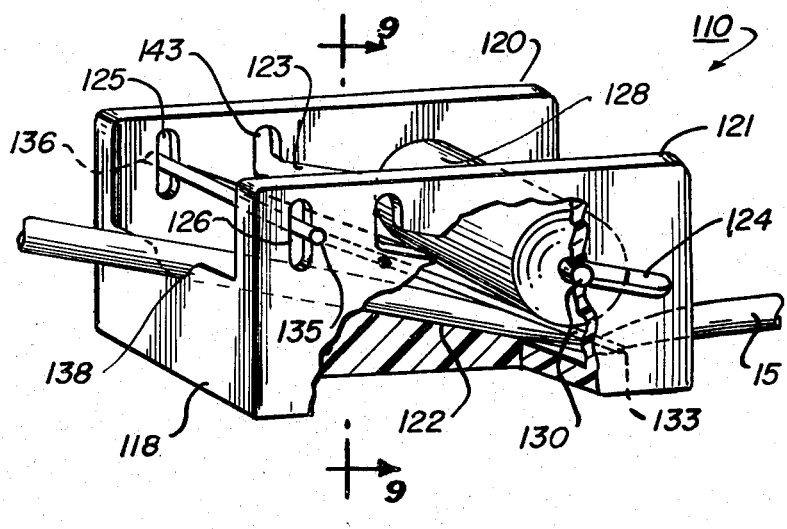
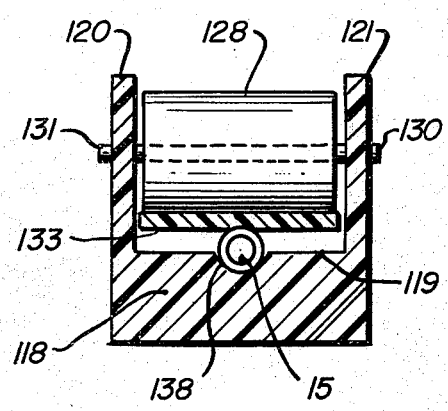

FLOW CONTROL DEVICE

BACKGROUND OF THE INVENTION

This invention relates to a flow control unit for accurately controlling the flow of fluid through a length of flexible tubing. More particularly, this invention relates to a combined clamp and flow control member which exerts a compressive force on a length of tubing over a wide area so as to prevent any permanent crimping of the tubing after the force is alleviated. The combined clamp and flow control member can completely compress the walls of the tubing so as to prevent fluid flow.

Clamping devices or fluid flow control units of the type concerned with in this invention are disclosed in U.S. Pat. Nos. 2,595,511 and 3,099,429. In these units, rollers are employed to exert an increasing or decreasing force upon flexible tubing so as to control the flow of fluid therethrough. The problem in employing clamps or flow regulating devices of these types is in the type of clamping action which a roller effects against a length of flexible tubing. When a roller contacts a length of tubing to compress it against a solid surface, the contact points on the roller compose a very small area at the circumference of the roller. The smaller the roller the more this is of a problem. In constructing a flow control unit to be used in conjunction with a parenteral solution unit large rollers are not practical. The prior art nowhere teaches a flow control device, and particularly of the disposable type, which is relatively small in construction yet can effect precise control of fluid through flexible tubing. Neither is there available a flow control unit which can serve as a combined clamp and flow control means which can be fabricated with a minimum number of parts and without costly molding techniques.

It is an advantage of the present invention to provide a combined clamp and flow control member which can precisely control the flow of fluid through flexible tubing without deforming the tubing for extensive periods of time after the compressive force is discontinued. Other advantages are a flow control unit which is disposable, employs a minimum number of parts, can be readily utilized with a single hand and can be fabricated without expensive molding procedures.

SUMMARY OF THE INVENTION

The foregoing advantages are accomplished and the shortcomings of the prior art are overcome by the present combined clamp and flow control member which has a clamp body defining a surface for supporting a length of flexible tubing and presenting a passage for the tubing. A platen is movably positioned between the walls of the clamp body for contacting the tubing. Guide surfaces are arranged in the walls with an axis positioned to intersect the axis of the supporting surface for the length of tubing. A rotatable member is positioned to be guided and rotated along the guide surfaces with the platen positioned between the rotatable member and the tubing. Upon movement of the rotatable member along the guide surfaces, it will contact the platen thereby compressing the tubing in a manner such that the compressive forces are distributed over a large area of the tubing. In a preferred manner, the clamp body has a base portion of substantially the same dimension in thickness or height over its entire length with the platen freely movable and rotatable in slots which if extended would intersect the base portion. The base portion has a V-shaped or U-shaped groove to position the tubing and better aid in its controlled constriction.

BRIEF DESCRIPTION OF THE DRAWINGS

A better understanding of the present combined clamp and flow control unit will be accomplished by reference to the drawings wherein:

FIG. 6 is an end view similar to that of FIG. 4 but showing an alternative base construction for the clamp body.

FIG. 7 is a top plan view of the base or floor of the clamp body shown in FIG. 6.

FIG. 8 is an alternative embodiment of the flow control device illustrating a base or floor constructed in an inclined plane.

FIG. 9 is a view in vertical section taken along line 9—9 of FIG. 8.

DESCRIPTION OF THE PREFERRED EMBODIMENT

Figure 2:
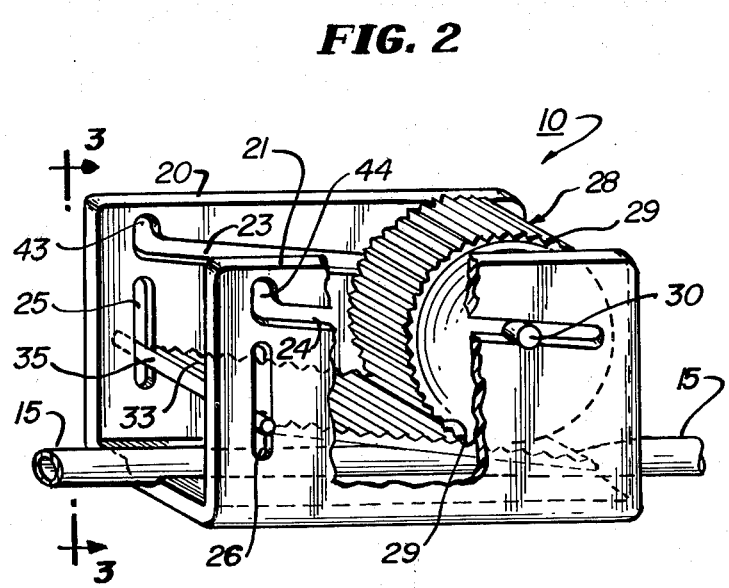
FIG. 2 is a perspective view of the control unit of this invention and with a portion broken away to better illustrate the rotatable member.
Figure 1:
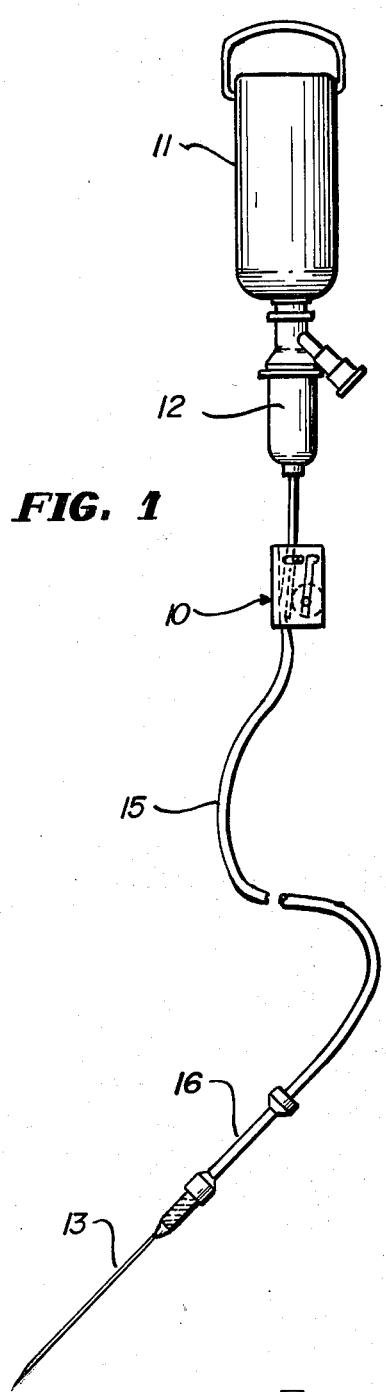
FIG. 1 is a view in side elevation illustrating the flow control clamp member operatively associated with a paraenteral administration unit.
Figure 3:
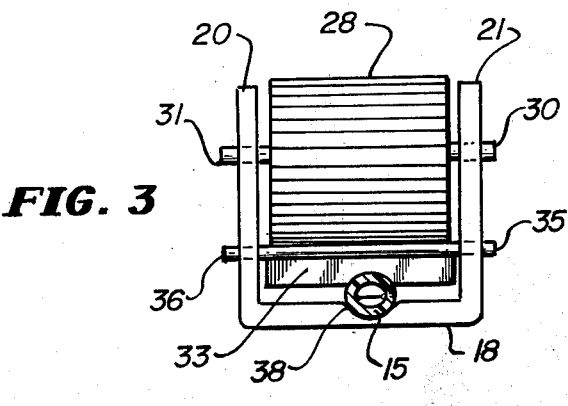
FIG. 3 is an end view taken along line 3—3 of FIG. 2.

Proceeding to a detailed description of a preferred embodiment of the present invention, the flow control device, generally 10, is shown for use in conjunction with a parenteral administration unit composed of a solution container 11 and a drip chamber 12 which is interconnected to a hypodermic needle 13 by means of a length of tubing 15 connected to needle adapter 16.

As best shown in FIG. 2, the combined flow control and clamp device 10 has a generally U-shaped body section with a base portion 18 for supporting a portion of the length of tubing 15. Extending from base 18 are opposing walls 20 and 21 which contain two pairs of parallel grooves or guide slots 23, 24 and 25, 26. Positioned in a movable manner between side walls 20 and 21 is a rotatable member in the form of a roller 28 which is guided along an intersecting axis with base 18 by means of pins 30 and 31. Movably disposed between roller 28 and tubing 15 is a platen 33 which slidably engages guide slots 25 and 26 by means of projections or bar members 36 and 35. It will be noted that slots 25 and 26 for the bar members 36 and 35 are positioned on an axis that is substantially perpendicular to base 18 so as to permit the free end portion of platen 33 to move in a direction toward and away from tubing 15 and at the same time to assume a pivotal position in the slots.

Figure 5:
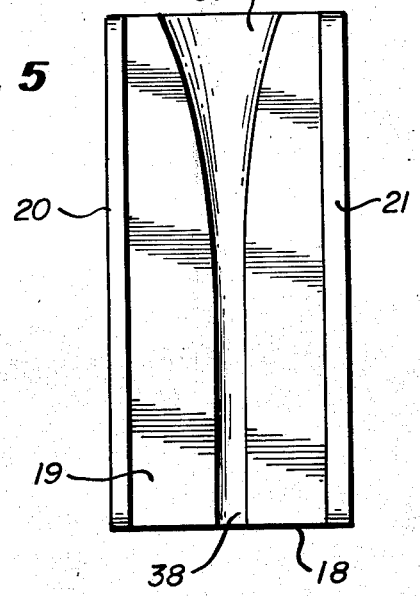
FIG. 5 is a top plan view of the base or floor of the clamp member shown in FIG. 2.
Figure 4:
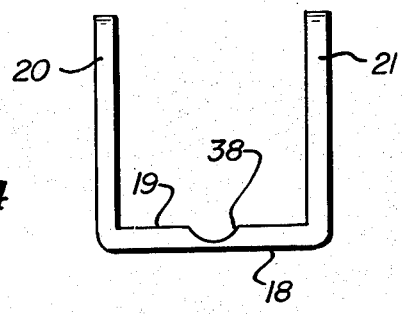
FIG. 4 is an end view of the wall structure of the clamp as shown in FIG. 2 and with all other parts removed illustrating a particular base construction.

With reference to FIGS. 4 and 5, it will be noted that base portion 18 has a U-shaped groove 38 which extends along its longitudinal axis and is U-shaped transversely to the supporting surface 19 as well as having a generally V-shaped portion 39 for permitting controlled compression of the tubing 15 which extends parallel to the supporting surface. An alternative modification of base 18 is shown in FIGS. 6 and 7 wherein in place of a U-shaped groove, a V-shaped groove 41 extends transversely to the supporting surface 19, the groove also having a generally V-shaped portion extending parallel to the supporting surface as indicated by the numeral 42.

Alternative Embodiment

FIGS. 8 and 9 represent an alternative embodiment of the flow control device with similar numbers in the "100" series being used to illustrate similar parts as in device 10. The main difference between flow control device 10 and 110 is in the design of the base portion 118. It will be noted that in unit 110, unlike base 18 which has the same dimension in height over its entire length, base 118 is in the form of an inclined plane with guide slots 123 and 124 constructed to guide roller 128 toward engagement of the base portion in the area approximately midway on the inclined plane surface as indicated by the numeral 122. In all other respects, the component parts of unit 110 are the same as unit 10 with the important element being the movable and slidable platen 133 which is positioned between roller 128 and tubing 15.

Operation

A better understanding of the advantages of flow control devices 10 and 110 will be had by a description of their operation. Referring to control device 10 first, it will have been previously assembled with platen 33 therein by inserting bar members 35 and 36 on platen in the respective guide slots 26 and 25. This can be effected by diagonally positioning the platen between the two slots and/or flexing the side walls 20 and 21 outwardly. Next, roller 28 with pins 30 and 31 will be positioned in guide slots 24 and 23, respectively, in a manner similarly described for inserting the platen in its guide slots. With the platen and roller thus assembled, and when it is desired to utilize clamp 10, a length of tubing 15 will be positioned on the base 18 and in groove 38 or 41. In order to accommodate the tubing 15, roller 28 will be positioned in or near the upwardly extending portions 43 and 44 of slots 23 and 24 respectively. In this position, the roller will either only slightly engage the platen 33 or will not contact it at all, so as to have no compressive force effected on tubing 15. When it is desired to control or restrict the flow of fluid in tubing 15, roller 28 will be moved in a direction away from the extending portions 43 and 44 in the slots thereby moving platen 33 toward the tubing and effecting a compressive force on it. In order to completely close off the flow of fluid in tubing 15, roller 28 will be moved in slots 23 and 24 to a position such that platen 33 will cause a complete collapse of the tubing walls. To permit flow of fluid in tubing 15 to resume or to incrementally increase the flow, the previously mentioned positioning of roller 28 is merely reversed in that the more the roller is moved in the direction of extensions 43 and 44 in the slots, the less compression will be effected on the tubing.

The operation of flow control unit 110 is basically similar to that described for unit 10 except that the movement of roller 128 along base 118 to decrease flow in the tubing or to completely stop it, is opposite. As roller 128 is moved in the direction of the extensions 143 and 144 of slots 123 and 124 respectively, it will effect a compression of the tubing walls and a complete collapse of it as the slots 123 and 124 are constructed with an intersecting axis at the higher dimension of the inclined base 118.

An important aspect of this invention is the utilization of platens 33 and 133 in combination with the rollers 28 and 128. The platens serve to distribute the compressive force of the rollers over a wide area of the tubing and thus prevent even a temporary indent or cold flow in the tubing which decreases the responsiveness of the clamp after the compressive force is alleviated. The utilization of the U-shaped and V-shaped grooves 38, 41, 39, 42 and 138 aid in accurate control in that they provide a single fluid or capillary channel and, in combination with the platen, positive positioning of the tubing is afforded beneath the platen while at the same time sharp surfaces are avoided so as to avoid any crimping of the tubing. This is particularly true of the U-shaped grooves 38 and 138. The purpose of having the generally V-shaped portions 39 and 42 of the grooves 38 and 41 is to afford a complete collapse of the tubing in these portions when the rollers 28 and 128 are in the positions closest to their respective bases 18 and 118.

It will be recognized that the various configurations for grooves 38, 39, 41 and 42 while being described for unit 10 can also be employed in unit 110 with the provision that the V-shaped portions 39 and 42 if utilized would be located at the highest dimension of the inclined base portion 118 adjacent slots 123 and 124.

While roller 28 is illustrated with a knurled or treaded surface 29 and, in a similar manner, is platen 33 for the purpose of providing traction, this surface could be modified and replaced with a roughened surface to provide frictional engagement or it could be eliminated. The same applies to roller 128 and platen 133. As described earlier, walls 20, 21 and 120, 121 can be flexed outwardly so as to effect the positioning of rollers 28 and 128 therebetween. This is accomplished by reason of the fact that the materials for fabricating the base portions 18 and 118 and their adjoining walls is a semirigid plastic material, preferably polypropylene. If desired, other polyolefin materials such as nylon, methylmethacrylate, etc. can be utilized. The flow control units 10 and 110 are completely disposable and consequently the platens 33, 133 and rollers 28, 128 with their respective guide bars are molded of a polyolefin plastic material and preferably nylon, high density polyethylene, polycarbonates, etc. While the guide bars or pins 30, 31, 35, 36 and 130, 131, 135, 136 are shown as freely engageable in their respective slots, these could be suitably flanged at their ends for a more permanent engagement.

It will thus be seen that through the present invention there is now provided a flow control unit which can effect precise flow control in a length of flexible tubing. No permanent or temporary crimping of the tubing is effected by the compressive force so that the tubing is immediately responsive to changes in clamping force. At the same moment, the clamp units can be easily fabricated and assembled without expensive molds or assembling procedures. The flow control units are completely disposable yet readily adapted to being operated by a single hand movement.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

I claim:

1. A tubing clamp for regulating flow of fluid through a length of flexible tubing comprising: a clamp body defining a surface for supporting a length of flexible tubing having a longitudinal axis, opposing walls extending from said surface and presenting a passage for said tubing, a platen pivotally mounted between said walls for contacting said tubing wherein the pivot axis is movable transversely to said tubing, guide surfaces arranged in said walls, a rotatable member positioned to be guided and rotated along said guide surfaces, said platen constructed and arranged to be movably positioned between said rotatable member and said tubing, said platen presenting a contact surface for said tubing substantially along and over the path of travel of said rotatable member, and cooperating with said rotatable member to exert an incremental compressive force on said tubing and by means of said platen to distribute the compressive force of said rotatable member over a wide area of said tubing including a substantial distance along its longitudinal axis.

2. The tubing clamp as defined in claim 1 wherein said surface for supporting said length of tubing is defined by a base portion of substantially the same dimension in thickness over its entire length.

3. The tubing clamp as defined in claim 1 wherein said rotatable member is a roller having pins and said guide surfaces are defined by grooves with said pins positioned in said grooves with said grooves having an axis positioned to intersect the axis of the supporting surface for the length of tubing.

4. The tubing clamp as defined in claim 1 wherein said platen is movably positioned in said clamp body by means of bar members extending from the platen and grooves disposed in said opposing walls and extending in an intersecting axis with said supporting surface with said bar members positioned in said grooves.

5. The tubing clamp as defined in claim 1 wherein said supporting surface has a groove extending along its longitudinal axis for accommodating said length of tubing.

6. The tubing clamp as defined in claim 5 wherein said groove is of a U-shaped configuration extending transversely to the supporting surface and having a V-shaped configuration parallel to the supporting surface.

7. The tubing clamp as defined in claim 5 wherein said groove is of a V-shaped configuration extending both transversely and parallel to the supporting surface.

8. The tubing clamp as defined in claim 1 wherein said surface for supporting said length of tubing is defined by a base portion presenting an inclined plane.

9. The tubing clamp as defined in claim 1 wherein said roller and said platen include a treaded surface.

10. A combined clamp and flow control member for regulating the flow of fluid through a length of flexible tubing comprising a generally U-shaped body section defining generally parallel wall members and an interconnecting base portion, said wall members defining a first pair of parallel grooves disposed to intersect, if extended, the plane of said base portion and a second pair of parallel grooves disposed, if extended, to substantially traverse the plane of said base portion, a platen having lateral projections extending in said second pair of parallel grooves, a roller member having pins extending in said first pair of parallel grooves, said first and second pairs of parallel grooves arranged to position said platen on said tubing and said roller member on said platen, said platen presenting a contact surface for said tubing substantially along the path of travel of said rotatable member, and cooperating with said rotatable member to distribute the compressive force of said roller member over a wide area of said tubing.

11. The combined clamp and flow control member as defined in claim 10 wherein said base portion for supporting said length of tubing is substantially the same thickness over its entire length.

12. The combined clamp and flow control member as defined in claim 10 wherein said base portion for supporting said length of tubing is formed by an inclined plane.

13. The combined clamp and flow control member as defined in claim 10 wherein said wall portion for supporting the length of flexible tubing has a groove extending along its longitudinal axis for accommodating said length of tubing.

14. The combined clamp and flow control member as defined in claim 13 wherein said groove is of a U-shaped configuration extending transversely to the supporting surface with a V-shaped configuration extending parallel to the supporting surface.

15. The combined clamp and flow control device as defined in claim 13 wherein said groove is of a V-shaped configuration extending both transversely and parallel to the supporting surface.

16. The combined clamp and flow control device as defined in claim 10 further including a parenteral administration unit operatively connected to said tubing including a solution container and drip chamber connected at one end and a hypodermic needle at the other.

* * * * *

UNITED STATES PATENT AND TRADEMARK OFFICE
CERTIFICATE OF CORRECTION

PATENT NO. : 3,960,149
DATED : June 1, 1976
INVENTOR(S) : Albert Frank Bujan

It is certified that error appears in the above-identified patent and that said Letters Patent are hereby corrected as shown below:

In Column 6, line 1 of Claim 9, please delete the numeral 1 and substitute therefor the numeral 3.

Signed and Sealed this twelfth Day of July 1977

[SEAL]

Attest:

RUTH C. MASON
*Attesting Officer*

C. MARSHALL DANN
*Commissioner of Patents and Trademarks*